United States Patent
Charlton et al.

(10) Patent No.: US 6,673,614 B2
(45) Date of Patent: Jan. 6, 2004

(54) RAPID METHODS AND KITS FOR DETECTION AND SEMI-QUANTITATION OF ANTI-ADENOVIRUS ANTIBODY

(75) Inventors: David Charlton, Redwood City, CA (US); Daniel R. Henderson, Palo Alto, CA (US)

(73) Assignee: Cell Genesys, Inc., San Francisco, CA (US)

( * ) Notice: Subject to any disclaimer, the term of this patent is extended or adjusted under 35 U.S.C. 154(b) by 0 days.

(21) Appl. No.: 09/894,510

(22) Filed: Jun. 27, 2001

(65) Prior Publication Data

US 2002/0015947 A1 Feb. 7, 2002

Related U.S. Application Data

(60) Provisional application No. 60/214,768, filed on Jun. 27, 2000.

(51) Int. Cl.[7] .......................... G01N 33/53; G01N 33/58; G01N 33/535; G01N 33/543; G01N 33/569
(52) U.S. Cl. ................... 435/975; 435/4; 435/5; 435/7.1; 435/7.9; 435/7.92; 435/7.94; 435/7.95; 436/828
(58) Field of Search ................. 435/975, 4, 5, 435/7.1, 7.9, 7.92, 7.93, 7.94, 7.95; 436/828

(56) References Cited

U.S. PATENT DOCUMENTS

| | | | |
|---|---|---|---|
| 4,366,241 A | 12/1982 | Tom et al. | |
| 4,962,023 A | * 10/1990 | Todd et al. | ............. 435/7 |
| 5,395,754 A | 3/1995 | Lambotte et al. | |
| 5,486,452 A | 1/1996 | Gordon et al. | |
| 5,587,285 A | 12/1996 | Cloyd et al. | |

FOREIGN PATENT DOCUMENTS

| | | | |
|---|---|---|---|
| EP | 402757 | 6/1990 | ......... G01N/33/543 |
| WO | WO 89/10980 | 11/1989 | ............ C12Q/1/68 |
| WO | WO 95/19434 | 7/1995 | ............ C12N/15/11 |
| WO | WO 97/01758 | 1/1997 | ......... G01N/33/537 |
| WO | WO 98/39464 | 9/1998 | ............ C12N/15/86 |
| WO | WO 98/39465 | 9/1998 | ............ C12N/15/86 |
| WO | WO 98/39466 | 9/1998 | ............ C12N/15/86 |
| WO | WO 98/39467 | 9/1998 | ............ C12N/15/86 |
| WO | WO 99/06576 | 2/1999 | ............ C12N/15/57 |
| WO | WO 00/15820 | 3/2000 | ............ C12N/15/86 |
| WO | WO 00/20041 | 4/2000 | ........... A61K/48/00 |
| WO | WO 01/73093 | 10/2001 | ............ C12N/15/86 |

OTHER PUBLICATIONS

Bischoff et al., "An Adenovirus Mutant That Replicates Selectively in p53–Deficient Human Tumor Cells," *Science*, vol. 274, pp. 373–376, 1996.

Bode et al., "Nitrocellulose–Enzyme–Linked Immunosorbent Assay (NC–Elisa)—A Sensitive Technique for the Rapid Visual Detection of Both Viral Antigens and Antibodies," *J. Virol. Methods*, vol. 8, 111–121, 1984.

Bramson et al., "Pre–Existing Immunity to Adenovirus Does Not Prevent Tumor Regression Following Intratumoral Administration of a Vector Expressing IL–12 but Inhibits Virus Dissemination," *Gene Therapy*, vol. 4, 1069–1076, 1997.

Christ et al., "Gene Therapy with Recombinant Ademovirus Vectors: Evaluation of the Host Immune Response," *Immunology Letters*, vol. 57, pp. 19–25, 1997.

Gahery–Segard et al., "Phase I Trial of Recombinant Adenovirus Gene Transfer in Lung Cancer," *J. Clin. Invest.*, vol. 100, pp. 2218–2226, 1997.

Heise et al., "ONYX–015, an E1B Gene–Attenuated Adenovirus, Causes Tumor–Specific Cytolysis and Antitumoral Efficacy That Can Be Augmented by Standard Chemotherapeutic Agents," *Nat. Med.*, vol. 3, pp. 639–645, 1997.

Ilan et al., "Oral Tolerization to Adenoviral Antigens Permits Long–Term Gene Expression Using Recombinant Adenoviral Vectors," *J. Clin. Invest.*, vol. 99, No. 5, pp. 1098–1106, 1997.

Kassler et al., "Performance of a Rapid, On–Site Human Immunodeficiency Virus Antibody Assay in a Public Health Setting," *J. Clin. Microbiol.*, vol. 33, pp. 2899–2902, 1995.

Lengyel, A. et al., "Latex Agglutination and Adenoviruses," *Acta Microbiol. Hung.*, vol. 39, Nos. 3–4, pp. 304, 308, 1992.

Petric, M. et al., "Detection of Adenovirus Antibody by Counterimmunoelectrophoresis," *J. Clin. Microbiol.*, vol. 10, No. 2, pp. 256–258, 1979.

Schulick et al., "Established Immunity Precludes Adenovirus–mediated Gene Transfer in Rat Carotid Arteries," *J. Clin. Invest.*, vol. 99, pp. 209–219, 1997.

Worgall et al., "Innate Immune Mechanisms dominate Elimination of Adenoviral Vectors Following In Vivo Administration," *Hum. Gene Ther.*, vol. 8, pp. 37–44, 1997.

Yang et al., "Cellular and Humoral Immune Responses to Viral Antigens Create Barriers to Lung–Directed Gene Therapy with Recombinant Adenoviruses," *J. Virol.*, vol. 69, pp. 2004–2015, 1995.

Zinkernagel, "Immunology Taught by Viruses," *Science*, vol. 271, pp. 173–178, 1996.

* cited by examiner

*Primary Examiner*—James Housel
*Assistant Examiner*—Bao Qun Li
(74) *Attorney, Agent, or Firm*—Linda Judge; Pamela J. Sherwood; Bozicevic, Field & Francis LLP (57) ABSTRACT

Methods for rapid detection and/or semi-quantitation of anti-adenovirus antibody are disclosed. Anti-adenovirus antibody is detected using a device comprising a membrane with adsorbed antigen which specifically binds anti-adenovirus antibody and an absorbent pad which is contacted with the membrane. By consolidating detection reactions in a confined location and eliminating the need to manually remove input reagents, detection and semi-quantitation is achieved rapidly and conveniently. The invention also provides kits and devices for detection and/or semi-quantitation of anti-adenovirus antibodies.

16 Claims, 1 Drawing Sheet

FIG. 1

RAPID METHODS AND KITS FOR DETECTION AND SEMI-QUANTITATION OF ANTI-ADENOVIRUS ANTIBODY

CROSS-REFERENCE TO RELATED APPLICATIONS

This application claims the priority benefit of the provisional patent application U.S. Ser. No. 60/214,768, filed June 27, 2000, which is incorporated herein by reference in its entirety.

TECHNICAL FIELD

This invention relates to the field of antibody detection, particularly rapid methods, devices and kits for detection and semi-quantitation of anti-adenovirus antibody.

BACKGROUND ART

The ability to detect antibodies to viruses such as adenovirus in a patient sample is increasingly becoming a prerequisite for optimal utilization of many modern health care technologies. This is especially relevant in two broad areas of health care: detection of infections based on presence of pathogen-specific antibodies, and "prepping" of patients for therapeutic agent administration.

The pathogenesis of the ubiquitous adenovirus is well-documented. Many relatively minor illnesses are associated with adenovirus infections, including acute febrile pharyngitis, pharyngoconjunctival fever, acute respiratory disease, pneumonia, epidemic keratoconjunctivitis, pertussis-like syndrome, acute hemorrhagic cystitis, gastroenteritis, hepatitis and persistence of virus in urinary tract. Fields, et al., Fields' VIROLOGY, Vol. 2, p. 2155 (3rd Ed.). A vaccine for the most severe of these diseases has been developed using a wild-type unattenuated replicating polyvalent vaccine comprised of adenovirus types 4 and 7.

Detection of anti-adenovirus antibodies is an important aspect of optimizing the administration, and hence therapeutic effects, of new therapeutic tools. This phenomenon results from two factors. First, many of the new therapeutic tools involve the use of adenoviral vector constructs. Second, it is now clear that the full potential of the virus-based therapeutic tools, specifically those that exploit the gene delivery advantages of adenovirus vector constructs, is hampered by the recipient's immune response.

Adenoviruses also form the basis of some of the most innovative and potentially powerful disease-fighting tools. One such tool is gene therapy, in which a defective gene or sequence is supplanted with an exogenous sequence. This approach holds great potential in treating not only cancer, but many other diseases as well, including cystic fibrosis, anemia, hemophilia, diabetes, Hungtington's disease, AIDS, abnormally high serum cholesterol levels, certain immune deficiencies, and many forms of cancer.

Gene therapy generally requires a delivery vehicle for the exogenous sequence, such as a viral vector. Recombinant adenovirus is one of the newly-developed viral agents that may be effective vectors against these diseases. For reviews, see Kim et al. (1996) Mol. Med. Today 12:519–527 and Smith et al. (1996) Gene Therapy 3:496–502.

In addition, in the cancer context, specific attenuated replication-competent viral vectors have been developed, in which selective replication in cancer cells preferentially destroys those cells. Various cell-specific replication-competent adenovirus constructs, which preferentially replicate (and thus destroy) certain cell types, are described in, for example, WO 95/19434, WO 98/39465, WO 98/39467, WO 98/39466, WO 99/06576, WO 98/39464, WO 00/15820. Another attenuated replication-competent adenovirus is Onyx-015 adenovirus. Onyx-015 has a deletion in the E1B-55kDa protein, which normally inhibits the cellular p53 tumor suppressor protein. Onyx-015 can replicate in p53-deficient human cells, but does not replicate efficiently in p53-positive cells. Bischoff et al. (1996) Science 274:373–376; Heise et al. (1997) Nat. Med. 3:639–645.

The favorable factors that make adenoviruses a safe therapeutic agent include: (a) infection with adenovirus has minor clinical disease manifestations; (b) adenovirus has a stable well-described and characterized genome; (c) adenovirus is unable to integrate its viral DNA into host DNA; (d) adenovirus allows transient gene expression; (e) adenovirus is able to infect both dividing and non-dividing cells; (f) adenovirus can infect a variety of human cell types; (g) adenovirus is physically stable; and (h) adenovirus is amenable to high titer production.

There are 47 different serotypes of adenovirus, which are distinguishable by antibody reactivity to epitopes on the virion surface. Each serotype is assigned to one of five Subgroups (A–E). Members of a Subgroup can exchange genetic material (recombine) efficiently, but they do not recombine with members of a different Subgroup. Adenovirus types 1, 2, 5, and 6 are members of Subgroup C. Adenovirus type 5 (the type typically used in gene therapy and for other therapies) is associated with a self-limiting, febrile respiratory illness and ocular disease in humans. In long-term immunosuppressed individuals, adenovirus-5 is also associated with renal impairment, hepatic necrosis, and gastric erosions. Shields et al. (1985) New England J. Med. 312:529–533; Zahradnik et al. (1980) Am. J. Med. 68: 725–732. Adenovirus-5 and the other Subgroup C viruses have little or no oncogenic potential in mammals. Horowitz (1990) in Virology, (Raven Press, New York, $2^{nd}$ Ed.) pp. 1679–1721.

While use of viral therapeutic agents such as adenovirus holds promise, there are a number of potentially significant barriers to their effectiveness. Two of the major limitations of virus-based vectors as therapeutic vehicles result from the subject's immune response to the presence of the viral agents, namely (a) the inactivation of virus by pre-existing circulating antibodies to the virus, and (b) the reduced efficacy of repeat dosage by primary or secondary induction of humoral immunity. For example, a recent serological survey indicates that 57% of the adult population in the U.S. has neutralizing antibodies to adenovirus-5 with titers ranging from 1:2 to 1:512. Schulick et al. (1997) J. Clin. Invest. 99:209–219. Neutralizing antibodies are generated to specific antigenic determinants within 7–14 days following intravenous adenovirus injection. Zinkernagel (1996) Science 271:173–178. These antibodies are typically specific for proteins on the virion, such as capsid proteins and various glycoproteins. George-Fries et al. (1984) Virology 134(1):64–71; Fisher et al. (1997) Nat. Med. 3(3): 306–12; Eing et al. (1989) J. Med. Virol. 27(1):59–65; Highlander et al. (1987) J. Virol. 61(11)3356–64; Durali et al. (1998) J. Virol. 72(5):3547–53. Activation of CD4+ lymphocytes by adenovirus capsid proteins also leads to the up-regulation of MHC class 1 molecules in infected cells contributing to the production of neutralizing antibodies as well as the clearing of adenovirus infected cells by CTLs. Yang et al. (1995) J. Virol. 69:2004–2015. For many patients, a therapeutic adenovirus will elicit an amnestic humoral response and a CTL response further decreasing the efficacy of repeat intravenous treatment with the same virus. Since the majority of the human population has been exposed to adenovirus during their lifetime, pre-existing immunity could be a major obstacle to the use of adenoviral vectors. Such high prevalence of neutralizing antibodies to adenovirus in adult humans could inhibit adenovirus dissemination (to distant tumor sites for example) and greatly limit the effectiveness of adenovirus-based therapy in vivo. More difficult to quantify is the potential non-neutralizing antibodies to inactivate adenovirus by opsonization.

The effect of antibodies on viral dissemination is a major issue in determining the success of viral therapy using parenteral administration, especially since intravenous administration may be desirable for treatment for metastatic disease. Although recent studies have indicated that pre-existing antibody may not reduce the efficiency of intratumoral viral administration (in terms of tumor regression), virus dissemination appears to be greatly impeded by pre-existing circulating antibodies. One group found that transgene expression in the liver of adenovirus-immune animals following intratumoral injection was reduced more than 1000-fold compared to the transgene expression found in n äive mice. Bramson et al. (1997) *Gene Therapy* 4:1069-1-76. In another example, in mice 90% of viral vectors is eliminated within 24 hours of intravenous injection. Worgall et al. (1997) *Hum. Gene Ther.* 8:37–44. This finding was confirmed by quantitative analysis of viral DNA in liver, spleen and lung using Southern analysis over the first 70 hours post injection demonstrating a 90% elimination of vector. Christ et al. (1997) *Immunology Letters* 57:19–25. Schulick et al. (1997) found that if rats are immunized by prior intravenous exposure to adenovirus, a second intravenous injection of an adenovirus vector gave no evidence of recombinant gene expression three days after the attempted gene transfer. This observation could be reproduced even in the presence of low (i.e., 1:2) titers of neutralizing antibody to adenovirus. Schulick et al. (1997). Another group examined immune responses to an adenoviral vector and to the recombinant gene expression (β-galactosidase protein) in four patients with lung cancer. Gahery-Segard et al. (1997) *J. Clin. Invest.* 100:2218–2226. In patient 1, a high level of neutralizing antibodies to adenovirus was detected before adenovirus-β-gal injection (100% neutralization at 1:400), whereas it was low in patient 3 (30% neutralization at 1:400) and undetectable in the other two patients. Virus DNA was detected by PCR in tumor biopsies on day 30 and day 60 from all patients except patient 1. Thus, recent studies have established that pre-existing humoral immunity poses a significant barrier to viral half-life, dissemination and effectiveness, and pre-existing anti-adenovirus neutralizing antibodies limit the therapeutic efficacy of adenovirus-mediated therapy through intravenous administration.

To address the problem of pre-existing immunity, various strategies have been developed. One strategy has been to down-regulate pre-existing anti-adenovirus immunity by oral tolerization based on administration of adenoviral proteins. Ilan et al. (1997) *J Clin. Invest.* 99(5):1098–1106. A potentially more effective and efficacious strategy is apheresis, which is a process by which certain blood components are removed extracorporeally and the blood is reintroduced into an individual, as described in PCT application WO 00/20041.

Apheresis can enhance performance of therapeutic viral vectors by partially pre-empting the body's immune defenses. This strategy, in turn, requires monitoring of humoral immunity before, during and after apheresis treatment. Towards that end, a rapid and convenient method for detection and/or semi-quantitation of anti-adenovirus antibody is particularly useful.

Numerous methods for detection and/or semi-quantitation of antibodies, including virus antibodies, are known. In the area of HIV (human immunodeficiency virus) antibody detection, published methods include a rapid enzyme immunoassay called Single Use Diagnostic System (SUDS) (see, e.g., Kassler, et al. (1995) *J. Clin. Microbiol.* 33:2899–2902; http://www.int-murex.com/virtop.htm; serological assays using non-denatured HIV antigenic determinants (U.S. Pat. No. 5,587,285); comb spotting detection using artificial synthetic polypeptide antigen (Chinese Patent Application No. 1195772); an assay based on pre-formation of a complex of antibody and enzyme-conjugated antibody binding protein (Austrian Patent Application No. 9400870); assay using polymer that has antigen fixed covalently to its surface through acid anhydride group (Japanese Patent Application No. A7012819); solid-phase assay for simultaneous detection of different antibodies (European Patent Application No. 402757); solid-phase immunoassay for simultaneous antigen and antibody detection (East German Patent Publication No. 272134); and an assay utilizing a non-human immune antibody reactive with an anti-human antibody as a positive control (PCT application WO 89/10980).

Various methods for detection and/or semi-quantitation of anti-adenovirus antibodies specifically are also known. One group has disclosed an enzyme-linked immunosorbent assay for the visual detection of adenoviral antibodies. Bode, et al. (1984) *J. Virol. Methods,* 8:111–121. The Bode method is based on immobilization of crude adenovirus preparations on nitrocellulose discs in microtitre plates. However, the method requires repetitive reagent additions to and removals from the reaction location, and the assay takes at least 4 hours to complete. Other methods include latex agglutination (e.g., Lengyel, A. et al. (1992) *Acta Microbiol. Hung.,* 39(3–4):303–8); simultaneous detection of more than one antibody by formation of complexes with labeled binding partner followed by capture on solid phase (WO 97/01758); and counterimmunoelectrophoresis (e.g., Petric, M. et al. (1979) *J. Clin. Microbiol.,* 10(2):256–8).

Other solid-phase immunoassays include general methods and apparatuses comprising solid support and absorbent material as described in U.S. Pat. Nos. 4,632,901 and 4,727,019. Neither of these publications discloses detection of anti-adenovirus antibodies with antigen adsorbed on solid support. U.S. Pat. No. 4,366,241 discloses concentrating zone method and apparatus for performing immunoassays. U.S. Pat. No. 5,486,452 discloses devices and kits for solid-phase immunoassays comprising a solid porous support where antigens or immunoglobulins are bound by direct application in a suitable geometry. U.S. Pat. No. 5,395,754 describes a membrane-based immunoassay method that includes having at least two sterically separate antigenic sites including at least one calibration zone.

It is clear from the foregoing discussion that rapid detection of anti-adenovirus antibodies in a subject sample is important and needed in monitoring, maximizing and ensuring efficacy of adenovirus-based therapy. The current invention provides rapid and convenient methods for detection and semi-quantitation of anti-adenovirus antibodies.

All patents, patent applications, and publications cited herein are hereby incorporated by reference in their entirety.

DISCLOSURE OF THE INVENTION

The present invention provides methods, devices and kits for detecting and/or semi-quantitating anti-adenovirus antibodies.

Accordingly, in one aspect, the invention provides a method for detecting anti-adenovirus antibody in a sample, comprising (a) contacting the sample (generally and usually a biological sample) with an antigen that specifically binds to anti-adenovirus antibody under conditions that permit formation of a stable antibody antigen complex, wherein the antigen is adsorbed on a membrane, and wherein the membrane is contacted with an absorbent; and (b) detecting any complex formed.

In one embodiment, the detection method comprises these steps: placing a wash buffer on the membrane; contacting a test sample with the pre-adsorbed antigen (i.e., antigen adsorbed on a membrane) to form a mixture of antigen and test sample; and sequentially placing a wash buffer, a detection molecule, and a wash buffer on the membrane.

Presence of anti-adenovirus antibody in the test sample is indicated by a detectable signal. In one embodiment, the membrane is a nitrocellulose paper-backed membrane. The absorbent is composed of material capable of absorbing, either by capillary action or otherwise, molecules that pass through the membrane. Preferably, the absorbent material is cellulose based. The test sample is any liquid that potentially contains anti-adenovirus antibody, the presence of which is to be determined with the invention. Preferably, the sample is plasma, serum or whole blood, for which detection of the presence of anti-adenovirus antibody is desired. The antigen is any substance that has antigenicity for anti-adenovirus antibodies. Adenoviruses are preferred. Even more preferred is whole/intact adenovirus, most preferably whole/intact adenovirus-5 (Ad5). Also preferred are adenovirus surface proteins. The detection molecule is any molecule that generates a detectable signal in the presence of anti-adenovirus antibodies. A preferred detection molecule is gold-conjugated Protein A comprising colloidal gold particles coated with protein A, BSA and PEG. Also preferred is to have the detection molecule in a buffer containing buffer, salts, protein, surfactant and preservative. Alternatively, the detection molecule is linked to an enzyme that is capable of catalyzing a chemical reaction that produces a detectable signal.

In another aspect, the invention provides a method for semi-quantitating anti-adenovirus antibody in a sample, comprising (a) contacting the sample with an antigen that specifically binds to anti-adenovirus antibody under conditions that permit formation of a stable antibody antigen complex, wherein the antigen is adsorbed at a membrane, and wherein the membrane is contacted with an absorbent; (b) detecting any complex formed; and (c) comparing a detectable signal, if any, of the antigen spot to a detectable signal of a reference sample spot, whereby anti-adenovirus antibody is semi-quantitated.

In one embodiment, the semi-quantitation method comprises these steps: placing a wash buffer on the membrane, contacting a test sample with the pre-adsorbed antigen; and sequentially placing a wash buffer, a detection molecule and a wash buffer on the membrane. Semiquantitation is achieved by comparing the signal intensities of antigen and reference sample spots. The reference sample is a substance that gives a detection signal equal or approximately equal to that of a known amount of anti-adenovirus antibody. Preferably, it is an antibody of the same Ig class or subclass as the anti-adenovirus antibody being semiquantitated. Human IgG is preferred. Other Ig's or subclasses are also preferred, including, but not limited to, IgE, IgA, IgD and IgM. The wash buffer, membrane and antigen are as described above for the detection method.

In another aspect, the invention provides devices for detection or semi-quantitation of anti-adenovirus antibody in a sample, comprising a membrane and an absorbent, wherein the membrane and absorbent are contacted with each other and wherein at least one antigen that specifically binds anti-adenovirus antibody is adsorbed on the membrane.

In another aspect, the invention provides kits for detection or semi-quantitation of anti-adenovirus antibody in a sample, comprising a membrane, an absorbent, and an antigen that specifically binds to anti-adenovirus antibody, said kit in suitable packaging. In one embodiment, the membrane and absorbent are contacted with each other. In another embodiment, at least one antigen is adsorbed on the membrane. In another embodiment, at least one antigen is provided separately. In yet another embodiment, at least one reference sample is adsorbed on the membrane. In still another embodiment, at least one reference sample is provided separately.

MODES FOR CARRYING OUT THE INVENTION

We have discovered methods, devices and kits useful for detecting and semi-quantitating anti-adenovirus antibodies in a rapid and convenient manner. By consolidating all chemical reactions necessary for detection and quantitation in a confined location on a solid surface, and eliminating the cumbersome procedures of manually removing input reagents, detection of anti-adenovirus antibody in a test sample is achieved rapidly, generally in less than 5 minutes, and conveniently. By including a reference sample containing a known amount of a substance that elicits a detection signal intensity that corresponds to a known amount of anti-adenovirus antibody, it is possible, by comparing signal intensities of test and reference samples, to obtain a semi-quantitative approximation of the amount of anti-adenovirus antibody in a test sample rapidly, generally in less than 5 minutes, and conveniently.

General Techniques

The practice of the present invention will employ, unless otherwise indicated, conventional techniques of cell biology, immunology, molecular biology, biochemistry, and adenovirus biology, all of which are within the skill of the art. Such techniques are explained fully in the literature, such as, "Antibodies: A Laboratory Manual," (Harlow, E. and Lane, D., 1988); "Physical Biochemistry: Applications to Biochemistry and Molecular Biology," second edition (Freifelder, D., 1982); "Handbook of Experimental Immunology," (D. M. Wei & C. C. Blackwell, eds); "Gene Transfer Vectors for Mammalian Cells," (J. M. Miller and M. P. Calos, eds. 1987); "Current Protocols in Immunology," (J. E. Coligan et al., eds., 1991); Felgner and Ringold (1989) *Nature* 337:387–388; Berkner and Sharp (1983) *Nucl. Acids Res.* 11:6003–6020; Graham (1984) *EMBO J.* 3:2917–2922; Bett et al. (1993) *J. Virology* 67:5911–5921; Bett et al. (1994) *Proc. Natl. Acad. Sci. USA* 91:8802–8806.

Definitions

An "antibody" (herein interchangeably used in plural form) as used herein is an immunoglobulin molecule capable of specific binding to a target, such as a polypeptide, through at least one antigen recognition site, located in the variable region of the immunoglobulin molecule. An antibody can be from any source of animal capable of producing them, for example, mouse, rat, rabbit or human. As used herein, the term encompasses not only intact antibodies, but also fragments thereof (such as Fab, Fab', F(ab')$_2$, Fv, single chain (ScFv)), mutants thereof, fusion proteins, humanized antibodies, and any other modified configuration of the immunoglobulin molecule that comprises an antigen recognition site of the required specificity. The term "antibody" includes polyclonal antibodies and monoclonal antibodies. The term also includes neutralizing antibodies, which include antibodies capable of diminishing or eliminating the normal or engineered activities of a molecule. The term also includes total antibodies capable of opsonization and/or anaphylaxis. An "anti-idiotype" antibody refers to a type of antibody that mimics the structure of an antigen to which another antibody is specific.

The term "anti-adenovirus antibody" as used herein refers to an antibody that specifically binds any substance that has an epitope or antigenic determinant recognized by antibodies that are induced as an immune response to exposure to adenoviral vector, adenovirus or parts thereof, or adenoviral anti-idiotype antibody. An anti-adenovirus antibody includes the antibodies as defined above under "antibody."

The term "antigen" as used herein is any substance that reacts in a demonstrable way with antibodies and/or immune cells. An antigen contains a determinant group within the molecule for the particular chemical group of another molecule that confers antigenic specificity. The term includes, but is not limited to, viruses (intact/whole), viral polypeptides, recombinant viral antigens, antigenic portions of a viral therapeutic vector (including the virus itself), a protein or other molecular structure containing an epitope specific to anti-viral vector antibody or anti-virus antibody, anti-idiotype antibodies specific for the anti-viral vector antibody or anti-virus antibody, and F' antibody fragments of the aforementioned antibodies. An antigen can be in purified form or mixed with at least one other component. An "adenovirus antigen" as used herein refers to an antigen that specifically binds to anti-adenovirus antibodies. The term includes, but is not limited to, adenovirus (intact/whole virus or parts thereof) and adenovirus polypeptides. An intact/whole adenovirus is an adenovirus in which the components normally found in an adenovirus are retained. This generally means the adenovirus has not been manipulated by methods that result in alteration(s) of the physical components of the virus. An adenovirus polypeptide is a polypeptide derived from or generated based on nucleotide and/or peptide sequence(s) of an adenovirus. The polypeptide can be a complete form of a polypeptide that is normally a part of an adenovirus, or a fragment thereof. Any moiety, whether or not adenovirus or derived from adenovirus which specifically binds to an anti-adenovirus antibody is an "adenovirus antigen."

An "antigen spot" is a discrete area on the membrane where at least one antigen is adsorbed; more than one antigen can be in a single antigen spot.

A substance is said to be "selective" or "specific" if it reacts or associates more frequently, more rapidly, or with greater duration with a particular cell or substance than it does with alternative cells or substances. For example, an antigen which "specifically" binds to anti-adenovirus antibody binds more frequently, more rapidly, with greater duration, with greater affinity, and/or with greater avidity than it binds to other antibodies. As such, an adenovirus antigen generally binds to the variable region of an anti-adenovirus antibody.

"Comprising" means including.

The term "test sample" or "sample" as used herein refers to any substance that potentially contains anti-adenovirus antibodies, for which detection or semi-quantitation of the antibody is desired. A test sample can be in any physical form so long as it allows antibody contained within it that is capable of reacting specifically with the antigen to do so. A test sample is preferably in liquid form. It includes, but is not limited to, blood, serum and plasma. "Blood" as used herein is bodily fluid including a cellular component and plasma, and can mean whole blood or a component thereof. "Serum" as used herein is bodily fluid that is a normal or pathological constituent of animal tissues, which is usually the yellowish protein-rich liquid which separates from coagulated blood. "Plasma" as used herein is the pale yellowish protein-rich liquid in which blood cells are suspended, and can also be the liquid component of lymph. "Samples" includes any biological sample, as described below.

The term "humoral immunity" as used herein refers to the presence of antibodies which specifically bind to adenovirus in an individual. These antibodies are elicited due to exposure to an immunogenic adenoviral agent, whether or not in the same form as the antigen component used in the invention.

The term "wash buffer" as used herein refers to any solution that is capable of reducing non-specific detection signal, preferably by at least about 10%, more preferably by at least about 25%, even more preferably by at least about 50%, even more preferably by at least about 75%, most preferably by at least 90%. "Non-specific detection signal" is generated when detection signal that is generated is not a true measure of amount of anti-adenovirus antibody bound to antigen on the membrane (and thus the amount of anti-adenovirus antibody in the test sample). Generally, wash buffer reduces non-specific detection signal by reducing the amount of extraneous material (including non-anti-adenovirus antibody and detection molecules that are non-specifically bound to the membrane) remaining on the membrane that might otherwise cause the generation of detection signal. The effect of wash buffer may be due to the ingredient(s) and/or physical washing. Preferably, the wash buffer solution comprises buffer, salts, protein, surfactant and preservative. Examples of wash buffers include HEPES and phosphate buffered solutions, with or without additional substances such as detergents or preservatives.

The "input surface of a (the) membrane" is the surface (side) of the membrane that is initially contacted with reagents and is generally the side on which antigen molecules are adsorbed. The "output surface of a (the) membrane" is the surface of the membrane that is not the input surface (i.e., opposite side of input surface).

As used herein, a "complex" is formed when an anti-adenovirus antibody is bound to an antigen.

The terms "absorbent," "absorbent pad" or "absorbent material" as used interchangeably herein refer to a material (s) that has a capacity and propensity to absorb liquid. It is preferably, but not necessarily, material that is capable of absorption by capillary action. Suitable material for the absorbent pad includes, but is not limited to, a cellulose-based material. It should be of a thickness that confers it with a capacity to trap most of the liquid that is used in practicing the invention, generally approximately 0.5 ml. Suitable thickness includes, but is not limited to, a thickness of preferably between about 0.05 inch and about 1 inch, more preferably between about 0.25 inch and about 0.75 inch, and most preferably between about 0.4 inch and about 0.6 inch.

The term "membrane with pre-adsorbed antigen," "membrane with adsorbed antigen," "adsorbed antigen" and other variations thereof, as used interchangeably herein refers to a membrane with antigen bound thereto that retains its antigenicity towards anti-adenovirus antibodies. Adsorption of the antigen is generally completed before the addition of test sample. An antigen is "adsorbed" if it cannot be substantially removed from the membrane through the procedures described herein. The antigen cannot be substantially removed if less than about 75% of the adsorbed antigen is released from the membrane through the procedures described herein, preferably less than 50%, even more preferably less than 25%, most preferably less than 10%.

The term "detection molecule" or "label" (interchangeably used herein) is any molecule capable of giving rise to a detectable signal that indicates the presence of anti-adenovirus antibody. A "detectable signal" is a signal that is either visible to the naked eye or detectable (readable) with the aid of an instrument, such as a spectrophotometer. Accordingly, detection may be by spectroscopic, photochemical, biochemical, immunochemical, or chemical means. Detection molecules are well known in the art for detection in immunoblotting, ELISA and other such assay techniques. Useful labels in the present invention include fluorescent dyes (e.g., fluorescein isothiocyanate, Texas red, rhodamine, green fluorescent protein and the like), radio-isotopes (e.g., $^3$H, $^{35}$S, $^{32}$P, $^{125}$I, or $^{14}$C), enzymes (e.g., LacZ, horseradish peroxidase, alkaline phosphatase, digoxigenin) and colorimetric labels such as colloidal gold or colored glass or plastic (e.g., polystyrene, polypropylene, latex, etc.) beads. A detection molecule can also be the anti-adenovirus antibody (if labeled) that is detected according to this invention. The label can be linked directly or indirectly to the anti-adenovirus antibody being detected according to methods well known in the art. Examples of indirect linkage include a ligand molecule (e.g., biotin) that is covalently bound to the anti-adenovirus antibody, in addition to binding to an anti-ligand (e.g., streptavidin) molecule which is either inherently detectable or covalently bound to a signal system, such as a detectable enzyme, fluorescent or chemiluminescent compound. Various anti-ligands and ligands can be used. In the case of a ligand that has a natural anti-ligand, such as biotin, thyroxine and cortisol, the ligand can be used in conjunction with labeled anti-ligands. Any haptenic or antigenic compound can be used in combination with an antibody. Molecules known to have a binding affinity for antibodies generally can also be used, such as Protein A, Protein G, and goat, horse, cow, rabbit or mouse anti-human IgG.

The term "protein A gold conjugate" as used herein refers to colloidal gold particles coated with protein A, that are preferably in a solution of at least buffer, salts, protein, surfactant and preservative. Examples of a buffer include phosphate buffer.

The term "enzyme-linked protein A" as used herein refers to protein A linked to at least one enzyme that is capable of catalyzing a chemical reaction that produces a detectable signal. These protein A molecules are preferably in a solution of at least buffer, salts, protein, surfactant and preservative. Examples of a buffer include phosphate buffer.

The term "semi-quantitating" as used herein refers to determining the approximate amount, preferably the concentration, of anti-adenovirus antibody in a test sample. "Approximate amount" refers to an amount that is preferably within about 50% of the precise amount, more preferably within about 25% of the precise amount, and most preferably within about 10% of the precise amount. Alternatively, "approximate amount" refers to a determination that the anti-adenovirus antibody amount in a test sample is above or below the amount(s) indicated by the reference sample(s).

The term "reference sample" as used herein is an amount of a substance that gives a detection signal equal to that of a known amount of anti-adenovirus antibody. The substance is preferably similar, more preferably identical, in molecular type (e.g. Ig class/subclass) and species of origin as the anti-adenovirus antibody (thought to be) in the test sample. The reference sample is generally, but not necessarily, pre-adsorbed on the membrane before the first wash buffer addition. A reference sample is "adsorbed" if it cannot be substantially removed from the membrane through the procedures described herein. A reference sample cannot be substantially removed if preferably less than 75% of the adsorbed reference sample is released from the membrane through the procedures described herein, more preferably less than 50%, even more preferably less than 25%, most preferably less than 10%. A "reference sample spot" is a discrete area on the membrane where at least one reference sample is adsorbed.

A "spot" of antigen or sample refers to adsorption onto a discrete area on a membrane.

The term "CsCl$_2$-purified adenovirus" as used herein refers to adenovirus obtained using CsCl$_2$ purification techniques generally known in the art.

An "individual" or "subject" as used herein is a vertebrate, preferably a mammal, preferably a human.

A "stable complex" is one that sufficiently persists after its formation to allow subsequent detection.

As used in the specification and claims, the singular form "a", "an" and "the" include plural references unless the context clearly dictates otherwise. For example, the term "a cell" includes a plurality of cells, including mixtures thereof.

Conditions that "allow" or "permit" an event to occur, such as formation of antigen antibody complex, are conditions that do not prevent such events from occurring. Thus, these conditions permit, enhance, facilitate, and/or are conducive to the event, such as binding of an antibody to an antigen. Such conditions, known in the art and described herein, depend upon the nature of the antibody as well as the antigen (i.e., degree of binding specificity of antibody to antigen). These conditions also depend on what event is desired, such as detection, expression or infection.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

Methods of the Invention

Methods for Detection of Anti-Adenovirus Antibody

The invention provides rapid and convenient methods for detecting anti-adenovirus antibody by consolidating requisite reactions in a confined location and eliminating the need to manually remove input reagents. Generally, anti-adenovirus antibody is detected by contacting a test sample with an antigen that specifically binds anti-adenovirus antibody under conditions that permit formation of a stable antibody antigen complex, wherein the antigen is adsorbed on a membrane, and wherein the membrane is contacted with an absorbent, and detecting any complex formed. Generally, these steps are accompanied by appropriate washing steps. More specifically, the methods generally entail the following steps: (a) placing a test sample on the adenovirus antigen which is pre-adsorbed on a membrane which in turn is contacted with an absorbent material; (b) washing the membrane with buffer (wash buffer); (c) if the anti-adenovirus antibody in the sample is not previously labeled, placing a solution of detection molecules on the membrane such that the detection molecules are contacted with antigen/antibody complex on the membrane; (d) washing the membrane with buffer; and (e) observing the resulting signal, if any, as indication of the presence of anti-adenovirus antibody in the test sample. The sample can be provided in volumes of preferably about 1 μl to about 100 μl, more preferably about 10 μl to about 75 μl, most preferably about 25 μl to about 60 μl. The wash buffer and detection molecule solution can each be provided in volumes of about 20 μl to about 200 μl, more preferably about 40 μl to about 180 μl, most preferably about 60 μl to about 140 μl.

The test sample is preferably a liquid that potentially contains anti-adenovirus antibody the detection of which is desired. Generally, serum, plasma or whole blood from the subject is used. However, any body fluid that is of a clarity or color that would not obscure the detection signal can be used. Methods of obtaining serum or plasma include, but are not limited to, standard veinipuncture techniques. Methods of obtaining whole blood include, but are not limited to, finger stick. Other test samples are obtained using standard techniques known in the art that substantially preserve preferably at least 50%, more preferably at least 75%, most preferably at least 90% of the antigen binding capacity and specificity of anti-adenovirus antibodies.

The antigen is preferably adenovirus, more preferably whole/intact adenovirus, even more preferably whole/intact adenovirus-5. It is understood that, for the purposes of this invention, one or more antigens may be used, i.e., a combination of different antigens or a single antigen. Antigens may be made using standard techniques in the art, such as chemical synthesis, recombinant techniques, purification of adenovirus or the generation of antigenic portions thereof.

In some embodiments, the antigen comprises an adenovirus polypeptide which comprises an epitope recognized by anti-adenovirus antibody. Examples of adenovirus polypeptide include, but are not limited to, surface polypeptides such as hexon, penton, and fiber, (intact, a portion, or a fusion thereof may be used). Any one or more (i.e., combinations) of adenovirus polypeptides may be used.

Membrane with Adsorbed Antigen

One or more antigens are adsorbed on the membrane, generally as a discrete spot. Antigen adsorption is achieved by techniques known in the art, which include, but are not limited to, placing antigen on a suitable membrane and allowing it to dry (for example, by air or vacuum drying). Antigen may be treated with a suitable material, such as glutaraldehyde, to aid in adsorption to a membrane. Membranes specifically pre-treated for covalent attachment of antigen may also be used. Suitable membranes include but are not limited to nylon membranes. Whichever adsorption technique is selected, care should be taken to ensure that antigenicity is not substantially reduced, preferably not more than about 50%, more preferably not more than about 25%, even more preferably not more than about 10%.

As an example, surface proteins and proteins that encapsulate the virion's genetic material are suitable for use in the preparation of antigens. Anti-adenovirus antibodies predominantly appear to be specific for either surface envelope proteins or capsid proteins, which also distinguish one serotype of a virus from another. Intact/whole adenovirus, intact/whole adenovirus polypeptides, fragments thereof, and fusion polypeptides containing at least an immunoreactive portion of a viral polypeptide may be used, as long as specific binding activity is present. Testing specific binding can be readily accomplished using standard binding assays in the art, such as ELISA or immunoprecipitation. Adenovirus has well-characterized surface and encapsulation proteins that may be suitable candidates as antigens.

Candidate polypeptides which would specifically bind to an anti-adenovirus neutralizing antibody are surface proteins. Non-enveloped adenoviral particles contain at least 11 different proteins (Maizel et al. (1968) *Virology* 36:115–125), but are composed primarily of hexon and penton capsomers. Fiber protein projects from the virion surface and makes the primary contacts with the cellular receptor, and variations in fiber protein sequence contribute to the tissue tropism of different adenovirus isolates. Arnberg et al. (1997) *Virology* 227:39–244. Neutralizing antibodies react to the type-specific antigenic determinants on the hexon and fiber polypeptides. Sequences of these adenovirus surface proteins are known in the art. See, e.g., Reubel et al. (1997) *Arch. Virol.* 142(6): 1193–212; Pring-Akerblom et al. (1995) *Res. Virol.* 146(6):383–388; Weber et al. (1994) *J. Gen. Virol.* 75:141–147.

Polypeptide antigens may be made using techniques standard in the art, such as synthetic and recombinant techniques. In addition to viruses and their various components, other candidates as antigens are anti-idiotype antibodies. Anti-idiotype antibodies mimic the structure of an antigen in their hypervariable regions. Anti-idiotype antibodies may be raised by using known anti-virus antibodies. An example of developing such antibodies is as follows: (1) inject a mouse with the adenoviral vector (adenovirus or fragments thereof) to induce production of anti-virus antibodies; (2) harvest B cells from the mouse using primary culture and fuse the cells with a myeloma cell line to make a hybridoma; (3) screen the hybridomas for production of anti-virus antibody by using an ELISA system with the corresponding adenoviral vector (adenovirus or fragments thereof) as a substrate; (4) grow up the clones that are positive for anti-virus activity and purify the antibodies; (5) inject the anti-virus antibodies in an adenoviral vector (or adenovirus or fragments thereof) naïve mouse to raise an immune response to the anti-virus antibodies thereby making the anti-idiotype antibody; (6) harvest B cells from the viral vector naïve mouse to make hybridomas; (7) screen the hybridomas for production of anti-idiotype antibodies that are specific to anti-virus antibodies; (8) grow up large amounts of the anti-idiotype antibody for use as an antigen. These antibodies may be used whole or in part as long as the fragments contain the region with the requisite specific binding activity.

The membrane is preferably a flat sheet, with a thickness that allows flow through of liquid. A preferred material is nitrocellulose paper. Other suitable material for the membranes is generally known in the art, and is commercially available from vendors such as Whatman. These materials include, but are not limited to, activated paper, nylon, activated nylon, polystyrene and polyacrylamide. "Antibodies: A Laboratory Manual," (Harlow, E. and Lane, D., 1988).

An absorbent is contacted with the output surface of the membrane so that it is capable of absorbing the solutions that pass through the membrane, such as wash buffers. The absorbent is composed of any material generally known to have high absorbent capacity, including, but not limited to, cellulose or derivatives thereof, and rayon, which are available commercially from vendors such as Whatman. In one embodiment, the absorbent is impregnated with a material that increases liquid absorption, such as silica gel, which can be in an amount of preferably between about 1% and 40%, more preferably between about 5% and 30%, and most preferably between about 10% and 20% of the weight of the absorbent pad.

Contacting the absorbent to the membrane is generally achieved by use of a suitable material in a manner that does not obstruct direct contact of the absorbent with the membrane. One way is to use adhesive tape to attach at least one side of the membrane-absorbent combination. Another way is to fit the membrane-absorbent combination into a form-fitting well. The membrane-absorbent combination can be fitted in a plastic housing (herein referred to as "sample well") that has an opening at one end that provides access to the antigen adsorbed on the membrane ("input surface"). The membrane-absorbent combination is positioned towards the bottom of the sample well. The fit of the membrane-absorbent combination in the sample well is tight enough to hold the membrane and absorbent in firm contact with each other so that liquid that is added onto the membrane is absorbed effectively through the membrane into the absorbent.

Detecting Anti-adenovirus Antibody

In the methods of the invention, anti-adenovirus antibody is detected by contacting a test sample with an antigen that is pre-adsorbed on the input surface of a membrane under conditions which permit formation of an antigen-antibody complex, which is in turn detected.

Generally, wash buffer is added to the membrane and allowed to absorb into the membrane. Test sample is then added onto the pre-adsorbed antigen spot on the membrane and allowed to absorb. Preferably, fresh samples are used. However, frozen samples can also be used. When frozen samples are used, they should be pre-treated according to standard procedures generally known in the art. For example, frozen samples are preferably thawed and mixed thoroughly and sediments allowed to settle out in a vertical position. This is followed with adding wash buffer, which is again allowed to absorb. If the anti-adenovirus antibody in the test sample is not previously labeled, detection molecules are added and allowed to absorb. Finally, wash buffer is added and allowed to absorb. Formation of the complex of antigen and anti-adenovirus antibody is allowed to proceed, generally less than about 10 minutes, preferably less than about 5 minutes, more preferably less than about 3 minutes, and most preferably less than 1 minute.

Any of a number of detection molecules may be used, including, but not limited to, protein A or antibodies that are conjugated to dye particles, enzyme, biotin, iodine or fluorochrome. Other detection molecules are provided in the definition above. Several commercially available detection molecules include, but are not limited to, protein A gold conjugates, horseradish peroxidase-conjugated protein A or anti-IgG antibody, and biotinylated protein A or anti-IgG antibody (biotinylated detection molecules require further treatment with anti-biotin antibody that are linked to enzymes or dye particles). Some detection molecules, such as protein A conjugated to dye particles, do not require further treatment to produce a signal, in which case a colorimetric signal would appear, after addition of detection molecules, specifically in the area of the antigen spot if the test sample contains anti-adenovirus antibody at or above the sensitivity threshold of the invention. Some detection molecules, such as enzyme-linked protein A or anti-IgG antibody, require further treatment, in which case the necessary reagents (substrates) that generate detectable signal upon catalysis by the linked enzyme are added following the final wash buffer step, following which a detectable signal results if the test sample contains anti-adenovirus antibody at or above the sensitivity threshold of the invention. "Antibodies: A Laboratory Manual," (Harlow, E. and Lane, D., 1988).

A preferred detection molecule is a protein A gold conjugate (interchangeably referred to herein as gold-conjugated protein A). Another preferred detection molecule is enzyme-linked protein A.

Yet another preferred detection molecule is anti-IgG antibody that is either conjugated with colloidal gold particles or enzyme. Certain labels, such as $^{125}I$ and fluorescent dyes, can also be conjugated directly according to methods known in the art to the anti-adenovirus antibody that is detected.

Detection of labels can be achieved by means well known in the art. Detection may be visual or by a suitable instrument appropriate to the particular label used, such as a spectrometer, fluorimeter, or microscope, as described in the definition of the term "label" above. For example, where the label is a radioisotope, detection can be achieved using, for example, a scintillation counter, or photographic film as in autoradiography. Where a fluorescent label is used, detection may be by exciting the fluorochrome with the appropriate wavelength of light and detecting the resulting fluorescence, such as by microscopy, visual inspection or photographic film. Where enzymatic labels are used, detection may be by providing appropriate substrates for the enzyme and detecting the resulting reaction product. Simple colorimetric labels can usually be detected by visual observation of the color associated with the label; for example, conjugated colloidal gold is often pink to reddish, and beads appear the color of the bead.

Methods for Semi Quantitation of Anti-Adenovirus Antibody

The invention also provides rapid and convenient detection methods for semi-quantitating anti-adenovirus antibody by consolidating the semi-quantitation reactions in a confined location, eliminating the need to manually remove input reagents, and utilizing at least one reference sample to provide quantitative reference data for semi-quantitation. Generally, anti-adenovirus antibody in a sample is semi-quantitated by (a) contacting a sample with an antigen that specifically binds to anti-adenovirus antibody under conditions that permit formation of a stable antibody antigen complex, wherein the antigen is adsorbed on a membrane, and wherein the membrane is contacted with an absorbent; (b) detecting any complex formed; and (c) comparing a detectable signal, if any, arising from the antigen-antibody complex to a detectable signal of (i.e., arising from) a reference sample spot, whereby anti-adenovirus antibody is semi-quantitated. Generally, these steps are accompanied by appropriate washing steps. More specifically, the methods generally entail the following steps: (a) washing a membrane that has at least one discrete spot of pre-adsorbed antigen and at least one discrete spot of pre-adsorbed reference sample with buffer; (b) placing a test sample on the pre-adsorbed antigen; (c) washing the membrane with buffer; (d) if the anti-adenovirus antibody in the sample is not previously labeled, placing a solution of detection molecules on the membrane; (e) washing the membrane with buffer; (f) observing the resulting signal, if any, as indication of the presence of anti-adenovirus antibody in the test sample; and (g) semi-quantitating the anti-adenovirus antibody of the test sample by comparing signal intensities of the antigen and reference sample spots (i.e., correlating the intensity of signal as reflecting the amount of complex in the sample with intensity of signal of reference sample(s)). The sample can be provided in volumes of preferably 1 $\mu$l to 100 $\mu$l, more preferably 10 $\mu$l to 75 $\mu$l, most preferably 25 $\mu$l to 60 $\mu$l. The wash buffer and detection molecule solution can each be provided in volumes of 20 $\mu$l to 200 $\mu$l, more preferably 40 $\mu$l to 180 $\mu$l, most preferably 60 $\mu$l to 140 $\mu$l.

Test samples and antigens used in the semi-quantitation method are as described above.

For the reference sample, any of a number of moieties may be used, so long as they share similar detection molecule binding characteristics as the anti-adenovirus antibody being semi-quantitated. For example, the reference sample may be an antibody, which may or not be adenovirus specific. Generally, IgG from the same species as the species of origin of the test sample is used. Adenovirus-specific immunoglobulin, where not commercially available, can be purified by standard techniques known in the art from blood, plasma or serum of adenovirus-immunized animals or humans. The amount (usually expressed as concentration) of the polypeptide in a reference sample is determined by standard techniques, which include, but are not limited to, Bradford, Coomassie and Lowry assays, and uv detection. "Antibodies: A Laboratory Manual," (Harlow, E. and Lane, D., 1988). In embodiments using non-adenovirus-specific immunoglobulin, purified samples are generally commercially available, from e.g., Calbiochem and Fluka. The amount of reference sample used is calibrated to give a detection signal equal to that of a known amount of anti-adenovirus antibody.

The reference sample(s) is generally, but not necessarily, pre-adsorbed on the same membrane that bears at least one antigen spot from the sample to be tested. In one embodiment, at least one reference sample is pre-adsorbed on the same membrane. In another embodiment, the reference sample is on a separate membrane that is subjected to similar, preferably identical, treatment as the membrane bearing the pre-adsorbed antigen. In yet another embodiment, the reference sample(s) is applied to, and allowed to adsorb on (similar to pre-adsorption of antigen), the membrane at a time point before addition of detection molecules.

Semi-quantitating Anti-Adenovirus Antibody

Anti-adenovirus antibody is semiquantitated by contacting a test sample with an antigen that is pre-adsorbed on a membrane that preferably also has at least one adsorbed reference sample (although as stated above, the reference sample could be on a separate membrane). The output surface of the membrane is in direct physical contact with an absorbent.

Wash buffer is added to a membrane that has pre-adsorbed on it at least one antigen and possibly at least one reference sample and is generally allowed to absorb into the membrane. Test sample is then added onto the pre-adsorbed antigen spot on the membrane and allowed to absorb, preferably completely. Wash buffer is added and allowed to absorb. If the anti-adenovirus antibody in the test sample is not previously labeled, detection molecules are added and allowed to absorb. If the anti-adenovirus antibody in the test sample is previously labeled (prior to contacting with antigen), the reference sample is preferably labeled prior to adsorption on the membrane. Formation of the complex of antigen and anti-adenovirus antibody is allowed to proceed, generally less than about 10 minutes, preferably less than about 5 minutes, more preferably less than about 3 minutes, and most preferably less than 1 minute. Finally, wash buffer is added and allowed to absorb.

By comparing the amount of signal or signal intensity, of the reference sample(s) and antigen spots, a semi-quantitative determination of the amount of anti-adenovirus antibody in the test sample is obtained. Semi-quantitation can be in the form of a determination of whether the test sample anti-adenovirus antibody amount is above or below the reference sample amount (based on signal intensities). Semi-quantitation can alternatively be based on a determination of the quantity range within which the test sample anti-adenovirus antibody amount lies by comparing antigen signal intensity with the intensities of two or more reference samples (the amount of the reference samples necessarily span the test sample anti-adenovirus antibody amount). Semi-quantitation amount can also be expressed in terms of being within a percentage range (+/-) of the amount of anti-adenovirus antibody indicated by the reference sample, such as, but not limited to about any of the following: 50%, 25%, 10% or 5% (for i.e., the amount of anti-adenovirus antibody in test sample x is within y % of z $\mu$g/ml (z is the amount of anti-adenovirus antibody to which the reference sample corresponds)).

Detection molecules and detection procedures are as described above.

In some embodiments, the invention is practiced as follows:

Reagents and Materials

Test Components

1. ADV CARD. A test card spotted with ADV (adenovirus) antigens and human IgG.
2. GOLD CONJUGATE. Colloidal gold protein-A conjugate in a buffer solution containing stabilizers and 0.2% sodium azide as preservative, stored at 2°–8° C.
3. BUFFER. A phosphate buffered solution with 0.2% sodium azide as preservative, stored at room temperature (below 32° C.).

Specimen Collection

Prepare serum or plasma from a whole blood sample, which has been obtained using proper venipuncture technique. Store samples at 2°–8° C. and assay within 24 hours. Freeze at −20° C. for no longer than 2 weeks, if the sample cannot be tested within 24 hours. Allow serum to reach room temperature before proceeding. Only serum and plasma samples that are clear are used. Cloudy samples may need to be cleared by centrifugation or filtration before testing. Samples that have a high fat content (gross lipemia) are not suitable. Fresh samples are recommended, however, frozen samples can be used. If a sample has been frozen, it is thawed mixed thoroughly and sediments allowed to settle out in a vertical position. Do not agitate the sample.

Procedure Notes

Allow all reagents, controls and samples to reach room temperature before testing.

1. Mix the conjugate gently before use.
2. When adding sample and reagents to the test card, allow to soak in completely before proceeding to next step.

3. Avoid the formation of bubbles or foam.

Procedure

1. Remove the ADV card from the foil pack.
2. Add 1 drop of BUFFER to the membrane of the sample well and allow to absorb completely.
3. Hold the sample pipette in a vertical position over the test card and deliver one drop (50 µl) of sample into the sample well.
4. Add 2 drops of BUFFER solution. Allow to absorb completely.
5. Add 2 drops of GOLD CONJUGATE. Allow to absorb completely.
6. Add 2–3 drops of BUFFER. Allow to absorb completely.
7. Read the result.

Interpretation of Results

1. Two red spots appearing on the membrane of the sample well indicates the presence of antibodies to adenovirus. The test and control spots should be clearly visible. If the test spot is darker than the control spot, then the level of antibody in the sample is equal to or greater than 12 µg/ml. If the test spot is equal to or lighter than the control spot, then the level of antibody is less than 12 µg/ml.
2. One red spot indicates a negative result. If a pink color develops over the surface of the membrane but without a discernable spot, the test is negative.
3. If no spots appear on the membrane then the test is invalid and must be repeated with a new card.

Kits and Devices of the Invention

The invention also includes kits for use in conjunction with the methods described herein. In one embodiment, the kits effect detection of anti-adenovirus antibodies. In another embodiment, the kits effect semi-quantitation of anti-adenovirus antibodies. These kits contain components that consolidate the detection and/or semi-quantitation reactions in one confined location and eliminate the need manually to remove input materials from the reaction location. These kits and compositions are useful for rapid and convenient detection and/or semi-quantitation of anti-adenovirus antibody in test samples, thus providing important information relating to infection status and for prognostic, diagnostic and therapeutic applications.

Kits of the invention comprise a membrane, adenovirus antigen (i.e., a moiety which specifically binds anti-adenovirus antibody) and an absorbent. Membrane and absorbent have been discussed above. The membrane and absorbent are preferably provided assembled with the output surface of the membrane contacting the absorbent. The membrane-absorbent pad combination may or may not be fitted in a plastic housing (well). In one embodiment, the antigen is pre-adsorbed on the membrane. In another embodiment, it is provided/packaged separately. In another embodiment, the kit includes wash buffer. An example of a wash buffer is a solution comprising buffer, salts, protein, surfactant and preservatives. In yet another embodiment, the wash buffer is HEPES buffer. The wash buffer that is included may or may not be pre-measured. Wash buffer has been discussed above. In some embodiments a HEPES buffer used for blocking and washing the membrane between sample and reagent additions is provided, preferably in a plastic dropper bottle for easy dispensing.

The kits of the invention may further comprise at least one kind of detection molecule. The detection molecule that is included may or may not be pre-measured. Detection molecules have been discussed above. In some embodiments, a preserved liquid colloidal protein-A gold conjugate used to obtain a visual test result is provided, preferably in a plastic dropper bottle for easy dispensing.

In some embodiments, disposal droppers are provided for sample, and/or buffer, and/or detection molecule addition.

The kits of the invention may further comprise at least one reference sample, provided either pre-adsorbed on the membrane, or separately. In one embodiment, a reference sample comprising human IgG is provided. In another embodiment, the reference sample comprises human IgG adjusted to provide a detection signal that corresponds to about 12 µg/mL of anti-adenovirus antibody in a test sample.

In yet another embodiment, the invention provides kits for detection or semi-quantitation of anti-adenovirus antibody in a sample, comprising nitrocellulose paper and a cellulose-based material, wherein the nitrocellulose paper and cellulose-based material are housed in a sample well, whole adenovirus-5 adsorbed on said nitrocellulose paper, HEPES buffer, gold-conjugated protein A and human IgG. In another embodiment, the human IgG provides a detection signal that corresponds to about 12 mg/mL of said anti-adenovirus antibody in said sample.

The kits of the invention may further comprise instructions for use. These instructions may be for using the components provided in the kit, for practicing the methods of the invention, or both. Accordingly, in some embodiments, the kits comprise instructions for detecting and/or semi-quantitating anti-adenovirus antibody in a sample. One exemplary set of instructions has been provided above.

The invention also provides devices for rapid and convenient detection and/or semi-quantitation of anti-adenovirus antibody, comprising a membrane contacting an absorbent. Adenovirus antigen is included, preferably pre-adsorbed on the input surface of the membrane. In the case of semi-quantitation, at least one reference sample is also included, either pre-adsorbed on the input surface of the membrane or provided separately. Membrane with pre-adsorbed antigen, with or without pre-adsorbed reference sample(s), absorbent, and reference sample have been discussed above.

In some embodiments, the invention provides a device comprising a plastic case or housing which contains an absorbent and membrane (which may or may not be contacted with each other), with the membrane spotted with an adenovirus antigen(s). Preferably, the device is a plastic case with a hinged top and bottom for ease of assembly. The top of the case has a sample well opening which is oval to accommodate the placement of an antigen spot and reference sample spot on the membrane of the assembled device. An absorbent is preferably die cut for exact placement into the plastic case. In some embodiments, the absorbent is a cellulose base to control flow and trap at least about 0.5 ml of fluid. Generally, the membrane (preferably nitrocellulose) is die cut in an irregular shape, to fit only one way into the plastic device to ensure proper placement during assembly. The adenovirus antigen mix is preferably optimized to detect antibodies to adenovirus, preferably comprising intact/whole adenovirus-5 and buffer. In some embodiments, the control antigen mix, preferably human IgG in buffer (preferably phosphate buffered solution, preferably including a preservative), is also spotted onto the membrane and used as a reference and to ensure the protein A gold conjugate is functioning.

An example of components of a device and/or kit (including packaging in a pouch) is as follows:
1. Bulk reagents
   Wash Buffer. PBS-Tween solution. The wash buffer and test device may be stored at 2–30° C.
   Gold Conjugate. Dilute protein A gold stock into conjugate buffer (phosphate buffered solution, preferably including a preservative) to approx. 2.5 OD/ml. The gold conjugate solution should be stored at 2–8° C. when not in use.
   Test Antigen: Adenovirus and/or recombinant antigens
   Control Antigen: Human IgG
2. Assembly of device
   Hinged pad printed plastic case
   Nitrocellulose membrane (1 cm×1 cm)
   Absorbent (0.75"×1.5")
3. Apply antigens to device
   0.5 µl spot of adenovirus antigen mix
   0.5 µl spot of control mix
4. Pouch device
   ½ gram desiccant
   foil pouch
   dropper
5. Fill gold conjugate and wash buffer into dropper bottles.

The following Examples are provided to illustrate but not limit the invention.

EXAMPLES

Illustrative Preparation of Membrane with Adsorbed Antigen

A nitrocellulose membrane was spotted and dried with 0.5 µl $CsCl_2$-purified adenovirus CN706 particles. CN706 is a recombinant adenovirus in which a prostate specific antigen transcriptional regulatory element (PSA-TRE) drives transcription of E1A. Rodriguez et al. (1997) *Cancer Research* 57:2559–2563. The CN706 particles were obtained as described in Rodriguez et al.

Illustrative Preparation of Membrane with Adsorbed Reference Sample

The appropriate amount of reference sample substance to use is a function of what the approximate or target amount of anti-adenovirus antibody in the test sample is.

The nitrocellulose membrane treated with CN706 particles were further spotted and dried with 0.5 µl of human IgG as the reference sample. The amount of human IgG in the reference sample was adjusted to give a signal equal to that of a patient sample containing about 12.5 µg/ml of antibody specific to adenovirus.

In this instance, the reference sample IgG amount was determined based on data showing that 80% of prostate cancer patients who had a neutralizing antibody titer less than 1:4 also had a total anti-adenovirus (Ad5) IgG of 12.5 µg/ml or less, as measured by the adenovirus neutralization assay described in Mastrangeli et al. (1996) *Hum. Gene Ther.* 7:79–97, and the enzyme-linked immunosorbent assay described in Molnar-Kimber et al., *Hum. Gene Ther.* (1998) 9:2121–2133. Thus, it was determined that for rapid clinical use in hormone refractory prostate cancer patients, a positive result at 12.5 µg/ml total anti-Ad5 antibody was an appropriate target (cut-off) value.

Illustrative Preparation of Device Comprising Membrane and Absorbent

A plastic case with a hinged top and bottom was used. The top of the case had a sample well opening which was oval to accommodate the placement of a test sample and reference sample on the membrane located in the case. An absorbent pad was die cut for exact placement into the plastic case. The pad was a cellulose-based absorbent material that was impregnated with silica gel (Multisorb Dessicants, Buffalo, N.Y.). The pad was prepared with dimensions that were greater than the membrane, such that a portion of the pad was not in physical contact with the membrane. The pad was approximately 3.5 cm by 1.75 cm. The dimensions were such that at least a portion of the liquid that flowed through the membrane into the portion of the pad that was in physical contact with the membrane would migrate laterally into the portion of the pad that was not in physical contact with the membrane. The absorbent functioned to control flow and to trap at least 0.5 ml of liquid. The nitrocellulose membrane was cut to dimensions of 1 cm by 1 cm and placed into the plastic case. This ensured proper placement in the case during assembly. This device was then used for adsorption of antigen and/or reference sample to the membrane contained therein and used for detection and/or semi-quantitation of anti-adenovirus antibody according to the method of the invention.

Illustrative Detection of Anti-Adenovirus Antibody

A nitrocellulose membrane-absorbent combination, prepared according to the method described above was used. The absorbent pulled liquid placed on the membrane through the membrane and into the absorbent by capillary action.

When applying samples and reagents to the membrane, care was taken to ensure that the added material soaked into the membrane completely before proceeding to the next step. Formation of bubbles or foam was avoided. Samples and reagents were allowed to reach room temperature before use.

HEPES buffer solution was prepared according to methods known in the art as the wash buffer and placed in a dropper bottle. One drop (about 50 µl) of the buffer was added to the input surface of the membrane. This was followed with one drop (about 50 µl) of patient serum. The serum was prepared from a whole blood sample, which had been obtained using proper venipuncture technique. If the samples could not be tested immediately, they were stored at 2°–8° C. and assayed within 24 hours. If the samples could not be tested within 24 hours, they were frozen at –20° C. for no longer than 2 weeks. The samples were allowed to reach room temperature before proceeding. For best results, only serum or plasma samples that were clear were used. Cloudy samples were cleared by methods known in the art, such as centrifugation or filtration.

Two drops (about 100 µl) of wash buffer were added, followed with two drops (about 100 µl) of colloidal gold protein A conjugate dissolved in a phosphate buffered solution. Finally, another two drops (about 100 µl) of wash buffer were added.

Presence of anti-adenovirus antibody in the patient serum was determined based on the appearance of a pink to reddish color/signal at the antigen spot that was above background ("background" is the color of the area of the nitrocellulose membrane not covered with antigen). If a pink color developed over the surface of the membrane but without a discernable spot at the antigen spot, the sample was deemed negative for anti-adenovirus antibody.

Completion time for the entire detection procedure was approximately five minutes.

Illustrative Semi-Quantitation of Anti-Adenovirus Antibody

A nitrocellulose membrane-absorbent combination, prepared according to the method described above was used. The absorbent pulled liquid placed on the membrane through the membrane and into the absorbent by capillary action.

Human IgG was used as reference sample. The amount of human IgG in the reference sample was adjusted to give a signal equal to a patient sample containing 12.5 μg/ml of antibody specific to adenovirus.

HEPES buffer solution was prepared according to methods known in the art as the wash buffer and placed in a dropper bottle. One drop (about 50 μl) of the buffer was added to the input surface of the membrane. This was followed with one drop (about 50 μl) of serum from a patient. The serum was prepared from a whole blood sample, which had been obtained using proper venipuncture technique.

Two drops (about 100 μl) of wash buffer were added, followed with two drops (about 100 μl) of colloidal gold protein A conjugate dissolved in a phosphate buffered solution. Finally, another two drops (about 100 μl) of wash buffer were added.

Figure 1:
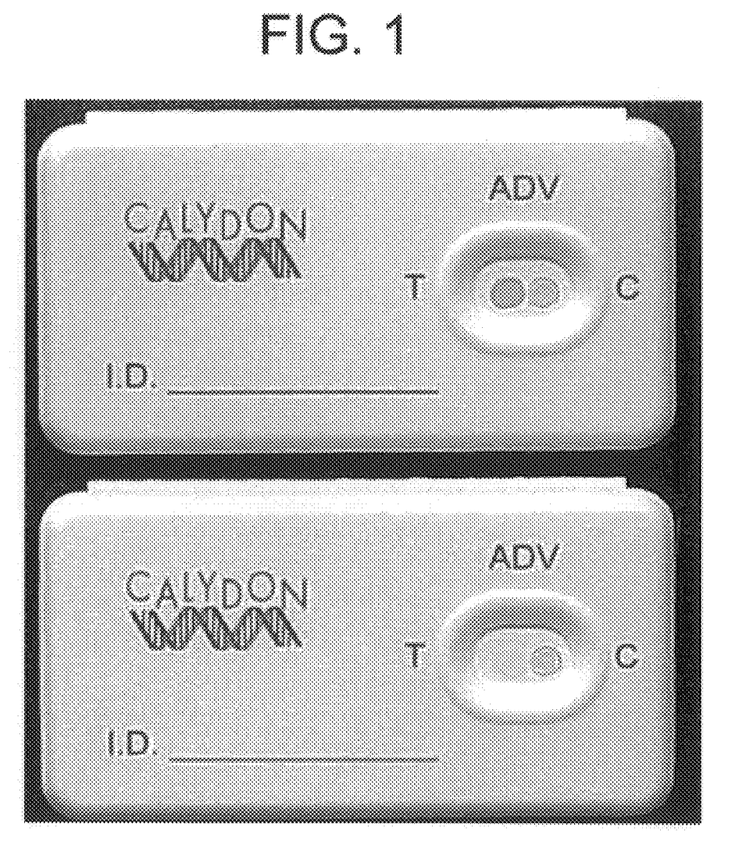
FIG. 1 shows the results of semi-quantitation of anti-adenovirus antibody on two nitrocellulose membrane-absorbent combinations prepared according to the Examples under "Illustrative Preparation of Membrane with Adsorbed Reference Sample." In each combination, the left spot (labeled "T") represents the antigen spot (containing adenovirus CN706 particles) and the right spot (labeled "C") represents the reference sample spot (containing human IgG adjusted to give a signal intensity equal to 12.5 $\mu$g/ml of anti-adenovirus antibody). In the upper combination, the signal intensity of the left spot is greater than the right spot, indicating that the test sample contained greater than 12.5 $\mu$g/ml of anti-adenovirus antibody. In the lower combination, the signal intensity of the left spot is less than the right spot, indicating a test sample concentration of anti-adenovirus antibody of less than 12.5 $\mu$g/ml.

Anti-adenovirus antibody concentration in the patient serum was determined by comparing the calorimetric intensities of the antigen and reference sample spots. Illustrative results are depicted in FIG. 1. Test samples that caused a color darker than that at the reference sample spot (upper combination) were deemed to contain anti-adenovirus antibody amounts at least equal to or greater than 12.5 μg/ml, while test samples that caused a color less intense than that at the reference sample spot (lower combination) were deemed to contain less than 12.5 μg/ml of anti-adenovirus antibody.

Completion time for the entire semi-quantitation procedure was approximately five minutes.

Although the foregoing invention has been described in some detail by way of illustration and example for purposes of clarity of understanding, it will be apparent to those skilled in the art that certain changes and modifications can be practiced. Therefore, the description and examples should not be construed as limiting the scope of the invention, which is delineated by the appended claims.

What is claimed is:

1. A kit for rapid detection or semi-quantitation of anti-adenovirus antibody in a sample, comprising a membrane, an absorbent pad in contact with the output surface of the membrane, and intact, whole adenovirus adsorbed to said membrane that specifically binds to anti-adenovirus antibody, said kit in suitable packaging.

2. The kit of claim 1, further comprising a reference sample consisting of a known amount of anti-adenovirus antibody.

3. The kit of claim 2, wherein said reference sample comprises human IgG.

4. The kit of claim 3, wherein the concentration of said human IgG is adjusted to provide a detection signal that corresponds to about 12 μg/mL of said anti-adenovirus antibody in said sample.

5. The kit of claim 1, further comprising at least one wash buffer.

6. The kit of claim 1, further comprising a detection molecule.

7. The kit of claim 1, wherein said membrane is nitrocellulose paper, and said absorbent is a cellulose-based material.

8. The kit of claim 1, wherein said membrane is nitrocellulose paper, said absorbent is a cellulose-based material, and said adenovirus is adenovirus-5.

9. The kit of claim 8, wherein said nitrocellulose paper and cellulose-based material are house in a sample well.

10. The kit of claim 8, further comprising wash buffer.

11. The kit of claim 10, wherein said wash buffer is HEPES buffer.

12. The kit of claim 8, further comprising gold-conjugated protein A.

13. The kit of claim 1, wherein said absorbent pad is a thickness sufficient to trap liquid used in a method of said rapid detection or semi-quantitation of anti-adenovirus antibody.

14. The method of claim 13, wherein said absorbent pad is about 0.4 to 0.6 inches in thickness.

15. A kit for detection or semi-quantitation of anti-adenovirus antibody in a sample, comprising nitrocellulose paper and a cellulose-based pad in contact with the output surface of the nitrocellulose paper, wherein the nitrocellulose paper and cellulose-based material are housed in a sample well, intact whole adenovirus-5 adsorbed on said nitrocellulose paper, HEPES 5 buffer, gold-conjugated protein A, and human IgG, said kit in suitable packaging.

16. The kit of claim 15 wherein the concentration of said human IgG is adjusted to provide a detection signal that corresponds to about 12 μg/mL of said anti-adenovirus antibody in said sample.

* * * * *